(12) United States Patent
Kiss et al.

(10) Patent No.: US 9,242,916 B2
(45) Date of Patent: Jan. 26, 2016

(54) PROCESS FOR PREPARING DICHLOROHYDRIN

(75) Inventors: Anton Alexandru Kiss, Arnhem (NL); Hendrik Jan Vos, Apeldoorn (NL); Eilertdina Henderika Renkema, Renkum (NL); Antoon Jacob Berend Ten Kate, Arnem (NL)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 780 days.

(21) Appl. No.: 13/380,972

(22) PCT Filed: Jul. 1, 2010

(86) PCT No.: PCT/EP2010/059326
§ 371 (c)(1),
(2), (4) Date: Dec. 27, 2011

(87) PCT Pub. No.: WO2011/000896
PCT Pub. Date: Jan. 6, 2011

(65) Prior Publication Data
US 2012/0108856 A1 May 3, 2012

Related U.S. Application Data

(60) Provisional application No. 61/223,190, filed on Jul. 6, 2009.

(30) Foreign Application Priority Data

Jul. 3, 2009 (EP) .................................... 09164486

(51) Int. Cl.
*C07C 29/82* (2006.01)

(52) U.S. Cl.
CPC ..................... *C07C 29/82* (2013.01)

(58) Field of Classification Search
CPC ........................................................ C07C 31/34
USPC .................................................. 568/841, 844
See application file for complete search history.

(56) References Cited

FOREIGN PATENT DOCUMENTS

| EP | 1 762 556 | 3/2007 |
|---|---|---|
| EP | 1 772 446 | 4/2007 |
| EP | 1 775 278 | 4/2007 |
| FR | 844375 | 7/1939 |
| WO | 2008/110588 | 9/2008 |
| WO | 2008/128004 | 10/2008 |
| WO | 2008/128005 | 10/2008 |
| WO | 2008/128010 | 10/2008 |
| WO | 2008/128013 | 10/2008 |
| WO | 2010/106085 | 9/2010 |

OTHER PUBLICATIONS

International Search Report for PCT/EP2010/059326, dated Sep. 7, 2010, 3 pages.
Kirk-Othmer Encyclopedia of Chemical Technology, "Distillation, Azeotropic, and Extractive", 2004, vol. 8, pp. 786-852.
Perry's Chemical Engineers' Handbook, $7^{th}$ edition, McGraw-Hill Companies, Inc., 1997, Chapter 13, pp. 13-1-13-108.
Bonner, Walter D., et al., "The Boiling Points of Constant Boiling Hydrochloric Acids", J. Am. Chem. Soc., May 1930, vol. 52, pp. 1747-1750.

*Primary Examiner* — Sudhakar Katakam
(74) *Attorney, Agent, or Firm* — Kenyon & Kenyon LLP

(57) ABSTRACT

The invention relates to a process wherein a stream comprising dichlorohydrin, water, and HCl is separated into a stream which is rich in dichlorohydrin and low in HCl and an aqueous HCl stream which is low in dichlorohydrin. The process involves the distillation of the mixture comprising dichlorohydrin, water, and HCl with an amount of water being added before and/or during the distillation such that the water concentration during the distillation is on the line D-E, or to the right thereof, in the phase diagram of FIG. 1.

20 Claims, 2 Drawing Sheets

PROCESS FOR PREPARING DICHLOROHYDRIN

REFERENCE TO RELATED APPLICATIONS

This application is the U.S. National Phase of PCT/EP2010/059326 filed on Jul. 1, 2010, and claims the benefit of U.S. Provisional Application No. 61/223,190, filed on Jul. 6, 2009.

The present invention relates to a process for preparing a dichlorohydrin stream which is particularly suitable for use in preparing epichlorohydrin. More in particular the invention relates to a process for preparing dichlorohydrin wherein a crude mixture containing HCl, water, and dichlorohydrin is treated such that an aqueous stream rich in dichlorohydrin and low in HCl is formed in a cost-efficient way. Further, it relates to a process wherein a valuable HCl-containing stream is obtained that is low in dichlorohydrin.

Processes for recovering dichlorohydrin are known. For instance, WO 2008/128004 describes a process wherein a phase comprising, inter alia, dichlorohydrin, water, and chlorinating agents is distilled or fractionated in step b) to separate a lower boiling (light) fraction comprising dichlorohydrins, water, and HCl and a higher boiling fraction (residue) which is essentially HCl-free (less than 0.01% HCl). In a next step c) a stripping agent, such as steam, is added to this residue to produce a vapour fraction comprising essentially stripping agent (water) and dichlorohydrin. In the theoretical examples various streams are predicted where 74.3 percent of the dichlorohydrin is retrieved through the vent and overhead, in combination with water and HCl, and 24.3 percent of the dichlorohydrin is retrieved in combination with water, by treatment of the residue.

Although the last theoretical stream is of a desired composition, which will separate into a dichlorohydrin-rich phase and an aqueous phase, both low in HCl, it is only a minor portion of the dichlorohydrin that can be made available in this form. The majority of the dichlorohydrin is in a mixture with HCl and water and cannot so easily be separated. More particularly, the separation of a water/dichlorohydrin mixture is often problematic in the presence of HCl, because the HCl tends to act as a solubilizer, resulting in a single phase dichlorohydrin/HCl/water mixture.

It is noted that EP 1 775 278 A1 discloses that 1,3-dichloropropane-2-ol forms a pseudoazeotrope with water and HCl and that such pseudoazeotropic systems cannot be easily separated by distillation. It teaches to distill a reaction product comprising glycerin, organic acid catalyst, reaction products, such as dichlorohydrin, HCl, heavy products, and water, such that the HCl concentration in the feed is lower than the HCl concentration of the binary azeotropic HCl/water composition. As a result a light aqueous fraction is formed that is low in dichlorohydrin and high in HCl and a fraction (liquid phase) is formed which still comprises the organic acid catalyst.

The presence of residual catalyst is undesired and the constant reflux of the reaction mixture is energy intensive. Also, the high amount of water has a negative impact on the reaction rate and the amount of water being refluxed is large.

EP 1 762 556 describes a process for separation of a mixture containing at least water, dichloropropanol, and hydrogen chloride wherein the mixture is separated in a distillation step wherein the sum of materials fed to said distillation step has a hydrogen chloride concentration which is lower than the hydrogen chloride concentration in the binary azeotropic composition hydrogen chloride/water at the pressure of the distillation. It is mentioned that it is possible to control the hydrogen chloride content in the sum of materials fed to the distillation step by adding water. Such addition can be carried out for example by injection of vapour into the boiler of a distillation column used in the distillation step or by recycling to the distillation step of a water phase which can be obtained for example by decantation of a fraction withdrawn from the top of a distillation column, or adding fresh water to the top of a distillation column or by adding a mixture of recycled and fresh water. It is furthermore mentioned that for instance, at atmospheric pressure, it is possible to obtain by distillation of the reactor gas phase a binary azeotropic mixture of water and dichloropropanol containing 23% by weight (% w/w) of dichloropropanol if the hydrogen chloride concentration in that gas phase in contact with the reaction medium is lower than about 20.22% w/w.

EP 1 762 556 does not contain a specific teaching on how to separate dichlorohydrin/HCl/water mixtures so that a dichlorohydrin stream is obtained which is low in hydrogen chloride and a hydrogen chloride stream which is low in dichlorohydrin.

The object of the present invention is to provide a process wherein the dichlorohydrin in a mixture comprising dichlorohydrin, HCl, and water is retrieved in the form of a dichlorohydrin stream that is low in HCl and wherein HCl is not wasted but obtained in a valuable and separate stream.

After extensive research efforts it was found that such a desired process can be obtained when adding a specific amount of water to the mixture comprising dichlorohydrin, HCl, and water, and distillation of the mixture, with the molar amount of water to be added to 1 mol of said mixture ($r_{H_2O/crude}$) being $$r_{H_2O/crude} \geq \frac{x_{DCH\text{-}crude}}{x_{DCH\text{-}az(DCH-H2O)}} + \frac{x_{HCl\text{-}crude}}{x_{HCl\text{-}az(HCl-H2O)}} - 1$$

with $x_{DCH.az(DCH-H2O)}$ being the molar fraction of dichlorohydrin in (heterogeneous) azeotrope of binary system dichlorohydrin-$H_2O$, $x_{DCH.crude}$ being the molar fraction of dichlorohydrin in the crude mixture, $x_{HCl.az(HCl-H2O)}$ being the molar fraction of HCl in (homogeneous) azeotrope of binary system HCl—$H_2O$, and $x_{HCl.crude}$ being the molar fraction of HCl in the crude mixture.

In that case and only in that case, the mixture can be split in a properly designed distillation unit into a first stream that is an aqueous HCl stream low in dichlorohydrin and a second stream that contains dichlorohydrin and water and is low in HCl. Depending on the composition of said second stream, it will typically separate, upon cooling, into an organic dichlorohydrin-rich phase and an aqueous phase comprising less dichlorohydrin.

It is noted that $r_{H_2O/crude}$ can be positive, negative or zero. A zero or negative value for $r_{H_2O/crude}$ means that no water needs to be added. It is even possible to extract water from the crude mixture (within the scope provided by the just-mentioned formula).

DETAILED DESCRIPTION

Figure 1:
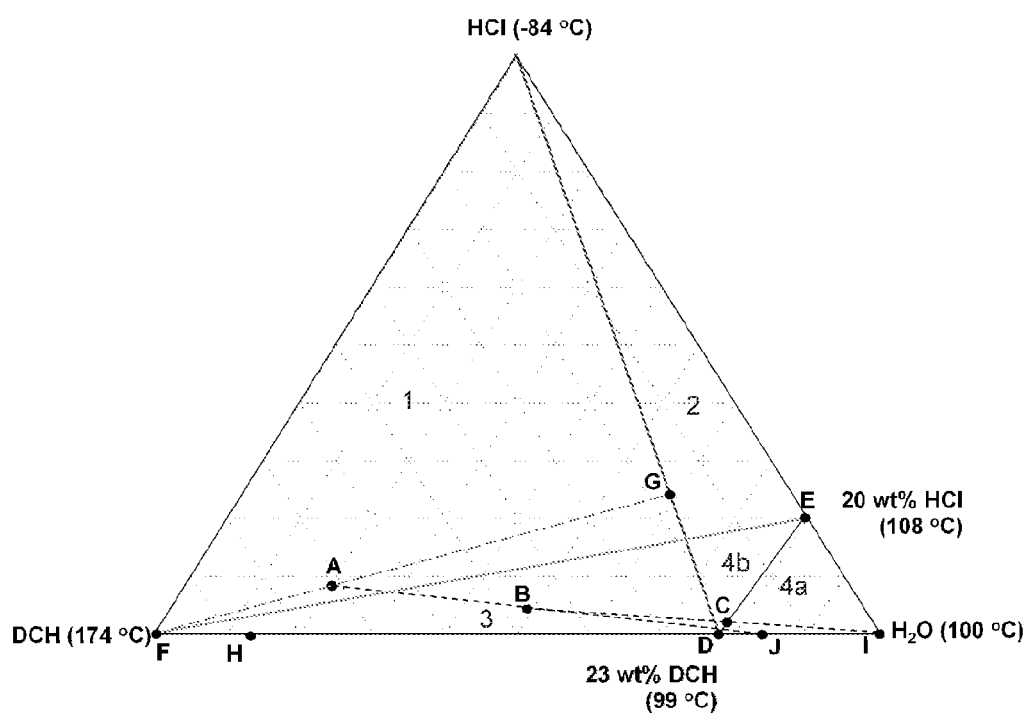
FIG. 1 shows a triangular diagram for the ternary mixture DCH—$H_2O$—HCl as a simple sketch based on pure component data and the compositions of binary azeotropes.

The mixture which is subjected to the separation process according to this invention (denoted throughout the description as "crude mixture") can be any mixture comprising DCH, HCl, and water. Said crude mixture can for example be obtained as the top product of a distillation column placed after a hydrochlorination reactor (such as distillation column DC1 and reactor R1, respectively, in FIG. 2). Optionally, it is mixed with a stream containing DCH and/or HCl from another source, e.g. the recycle stream from a liquid-liquid separator (see such as LLS1 in FIG. 2) It is to said crude mixture that water is supplied to achieve the desired separation.

It is noted that common general knowledge provides the skilled person with enough tools to find the distillation conditions leading to the optimum separation between DCH and HCl (see for example *Perry's Chemical Engineers' Handbook*, 7$^{th}$ Ed, The McGraw-Hill Companies, Inc. 1997, Chapter 13). He may for example vary the size of the distillation column and/or change the reflux ratio.

The present invention furthermore relates to a process wherein the reaction mixture of the reaction of glycerin and HCl to form dichlorohydrin is separated, in an economic fashion, into a dichlorohydrin stream that is low in HCl. Preferably, the amount of water in the reaction is kept to a minimum, as water will slow down the reaction rate. The amount of water which is added in order to perform the separation process according to the present invention is preferably as low as possible to reduce energy costs and environmental burden. Said process comprises several steps. The first step is conventional and comprises the contacting, in a conventional reactor, of glycerin and HCl, optionally in the presence of a catalyst, with the formation of dichlorohydrin, followed by a first distillation step wherein dichlorohydrin, water, and HCl are distilled off (as the light fraction) in a conventional way, the bottoms optionally being recycled wholly or partly, followed by a step wherein water is added to said light fraction, being a mixture comprising dichlorohydrin, water, and HCl, and distillation of this mixture in a second distillation step in which an aqueous HCl-containing stream that is low in dichlorohydrin and a stream which is high in dichlorohydrin and low in HCl are formed. The step wherein water is added and the second distillation step may be simultaneous, meaning that water is added in the distillation equipment, or the water may be added before the mixture is fed to said distillation equipment, or a combination of both.

It is noted that the stream high in dichlorohydrin and low in HCl will contain water. Due to the fact that little HCl is present in the mixture, this stream will easily separate into a stream rich in dichlorohydrin and low in water and an aqueous stream with less dichlorohydrin.

The bottoms of the first distillation will contain heavies and, if used, preferably the catalyst.

The process of the invention has various advantages over the processes as presented in the prior art. More specifically, the process of claim 1 defines the process which is believed to have the lowest possible energy requirement per unit of dichlorohydrin produced in the organic dichlorohydrin-rich phase. More specifically, the optimal amount of water to be added prior to or during the distillation step of the mixture comprising dichlorohydrin, water, and HCl is now defined, presenting the optimal operation of the distillation unit, i.e. the minimum required amount of water to be used, which minimizes the energy requirements of said distillation unit. Further the addition of the appropriate amount of water in accordance with the invention was found to be the only distillation region where it is possible to separate a mixture of dichlorohydrin, HCl, and water into a dichlorohydrin-rich stream that is low in HCl and a HCl-containing stream low in dichlorohydrin in a single distillation step. Contrary to many processes in the prior art, the so-obtained HCl-rich stream (which in our case is essentially free of dichlorohydrin) is valuable. So there are two valuable streams from the process, a concentrated clean dichlorohydrin stream and a concentrated hydrochloric acid solution low in dichlorohydrin.

The process starting from glycerin and HCl allows the retrieval of large amounts of unreacted raw materials, intermediates, and catalysts immediately after the reaction step in a first distillation step. As a result, such products do not contribute to the energy required in the second distillation step wherein the mixture comprising dichlorohydrin, water, and HCl is separated.

Also, in the process starting from glycerin and HCl, the two separation steps (see DC1 and DC2 in FIG. 2) can be conducted at two distinct pressures, with a low pressure in DC1 being found to reduce byproduct formation due to degradation of organic species, and the high pressure in DC2 being found to shift the azeotrope to a dichlorohydrin-rich composition, meaning less water is evaporated, reducing the size of the recycle streams, the size of the apparatus, and energy costs.

Further, in the process starting from glycerin and HCl, the amount of water in the reactor can be kept at a minimum, which has the advantage that the reaction rate is kept at a maximum and the catalyst is predominantly present in its active form (i.e. the ester form with raw materials and intermediates), which is less volatile than the acid form, improving the efficiency of the separation step wherein the reaction mixture is separated into a vent, light liquid, and heavy fraction (DC1). It is noted that due to the reaction between HCl and glycerin, water is formed. Therefore there will always be some water present.

As an example of the benefit obtained using the dichlorohydrin according to the invention, it is presented that in typical use of dichlorohydrin, the production of epichlorohydrin, it is avoided that the HCl present in the dichlorohydrin must be neutralized and less waste is produced. More particularly, in the production of epichlorohydrin (ECH), dichlorohydrin is reacted with alkaline, such as NaOH. The removal of HCl reduces the consumption of alkaline in the ECH process and leads to the production of less salt, such as NaCl, in that process, leading to smaller waste streams in the ECH process.

It is noted that throughout this document, the term "low in HCl" means less than 5% w/w, preferably less than 2% w/w, and more preferably less than 1.5% w/w is present, most preferably less than 0.5% w/w, down to as little as 1 mg/kg HCl. The term HCl-containing means more than 0.02% w/w HCl, preferably more than 0.05% w/w HCl, and more preferably more than 0.5% w/w HCl, up to as much as 50% w/w HCl.

The term "low in dichlorohydrin" means less than 10% w/w, preferably less than 1% w/w, most preferably less than 0.1% w/w dichlorohydrin, down to as little as 1 mg/kg dichlorohydrin. The term "high in dichlorohydrin" means more than 20% w/w dichlorohydrin. For instance, the stream coming from the distiller wherein the mixture comprising dichlorohydrin, water, and HCl is separated in accordance with the invention was found to typically contain between 15, preferably 20, and 30% w/w of dichlorohydrin. However, after the liquid/liquid separation of this very stream into an organic and an aqueous phase, the organic stream high in dichlorohydrin was found to contain between 70 and 90% w/w of dichlorohydrin.

All of the weight percentages are based on the total weight of the stream to which the numbers relate.

The dichlorohydrin of the invention can exist in the form of various isomers of dichloropropanol. Typically it is a mixture of isomers consisting essentially of 1,3-dichloropropane-2-ol and of 2,3-dichloropropane-1-ol. In a preferred embodiment the major isomer obtained according to the present process is 1,3-dichloropropane-2-ol. However, both isomers are suitable as starting product for a dehydrochlorination with a view to producing epichlorohydrin and/or epoxy resins. The dichlorohydrin of the invention suitably comprises from 10 to 100% w/w of dichloropropanol. It preferably comprises from 50 to 95% w/w of dichloropropanol.

The glycerin, also known as glycerol, used in embodiments of the invention can be obtained from renewable raw materials, or synthesized from natural oil resources. The glycerol derived from renewable raw materials can be used in the crude form or after conventional purification. The term "glycerin obtained from renewable raw materials" is intended to denote in particular glycerin obtained in the course of the production of biodiesel, or else glycerol obtained during the conversion of fats or oils of plant or animal origin in general, such as saponification, trans-esterification or hydrolysis reactions. A particularly suitable glycerin can be obtained during the conversion of animal fats. Another particularly suitable glycerin can be obtained during the production of biodiesel. In contrast, synthetic glycerin is generally obtained from petrochemical resources. The glycerin can be a crude product or a purified product. When the glycerol is a crude product, it can comprise, for example, water and a metal salt, in particular a metal chloride, which is preferably chosen from NaCl and KCl. The metal salt can also be selected from metal sulphates such as sodium sulphate and potassium sulphate. The crude product can also contain organic impurities such as carbonyl compounds, in particular aldehydes, fatty acids, or esters of fatty acids, such as in particular monoglycerides or diglycerides, optionally in combination with water and/or the metal chloride. A typical crude glycerin comprises at least 40% w/w of glycerin, preferably at least 50% w/w and more preferably at least 70% w/w of glycerin. The crude glycerin typically comprises at most 99% w/w but it often comprises at most 95% w/w of glycerin. When purified glycerin is used in the use according to the invention, said glycerin is obtained, starting with the crude product, by means of one or more purification operations such as a distillation, an evaporation, an extraction, or else a concentration operation followed by a separation operation such as settling out, filtration or centrifugation. A suitable grade of glycerin comprises 50 to 99.9% w/w of glycerin.

Preferably the amount of water in the glycerin is less than 20% w/w, more preferably less than 10% w/w, even more preferably less than 5% w/w, and most preferably less than 3% w/w of water, since the water introduced with the glycerin was found to slow down the reaction with HCl while also increasing the energy intensity of the process, since the water will be distilled in the process of the invention.

In the process for making dichlorohydrin according to the invention, the chlorinating agent may be an agent for oxidative chlorination or substitutive chlorination. An agent for substitutive chlorination is preferred. Oxidative chlorination agents include chlorine. Most preferred is the use of a substitutive chlorination agent, particularly hydrogen chloride. The hydrogen chloride may be in the form of an aqueous solution of hydrogen chloride. In this case, the hydrogen chloride content of the solution is generally at least 4% w/w. Preferably, this content is greater than or equal to 20% w/w. The hydrogen chloride content of an aqueous solution is generally at most 37% w/w.

The HCl may be a low-quality hydrochloric acid derived, for example, from the pyrolysis of chlorinated organic compounds or have been used for stripping metals. In particular, it is possible to use hydrochloric acid loaded with dichloropropanol originating, for example, from a reaction for producing dichloropropanol by hypochlorination of allyl chloride, according to the usual process for synthesizing this product. In a preferred embodiment concentrated hydrochloric acid, generally comprising from 28 to 37% w/w of hydrogen chloride, is used as a primary source of the chlorinating agent, and said concentrated hydrochloric acid is separated, for example by evaporation, into at least two fractions, the first consisting essentially of anhydrous hydrogen chloride and the second comprising hydrogen chloride and water in proportions in which they form an azeotrope, said azeotrope consisting, at a pressure of 101.3 kPa, of 19 to 25% of hydrogen chloride and of 75 to 81% w/w of water, in particular of approximately 20% w/w of hydrogen chloride and of approximately 80% of water.

In another embodiment the chlorinating agent is hydrogen chloride which is generated in situ within the reaction medium, for example starting with an inorganic acid such as sulphuric acid or phosphoric acid, and a suitable metal chloride such as NaCl, KCl or $CaCl_2$.

These various embodiments can be combined; thus, for example, a supply of aqueous HCl can be completed with a supply of gaseous and/or anhydrous HCl.

A high concentration of HCl in the reactor will increase the reaction rate. Consequently it is preferred to lower the amount of water (which according to an unproven theory will dissociate HCl, making it less efficient as a chlorinating agent) and maximize the HCl concentration in the reaction mixture. Accordingly, it may be preferred to use anhydrous HCl. Typically such dry HCl is supplied in the gaseous form. When anhydrous HCl is used, it is preferred to direct a liquid stream comprising the glycerol against the current of the stream of HCl. The HCl is advantageously dried before use, for example by adsorption on a suitable solid, such as a molecular sieve, or by reverse osmosis through a suitable membrane.

In the step wherein glycerin and HCl are reacted the reaction medium typically comprises from 1 to 50% w/w of water. This is partially reaction water, as explained above, and partially the water that was introduced with the glycerin and/or the HCl. Preferably the reaction mixture comprises from 1 to 15% w/w of water, more preferably at most 10% w/w of water, and most preferably up to 5% w/w of water.

In the process for producing dichlorohydrin according to the invention, the reaction between the glycerol and the chlorinating agent may be carried out in the presence or in the absence of any conventional catalyst. It is preferred to carry out the reaction in the presence of a suitable catalyst. Preferred catalysts are those that are easily separated from a mixture of dichlorohydrin, water, and HCl by distillation. Most preferably the catalyst remains in the heavy fraction of such a distillation.

In one embodiment, the catalyst is a carboxylic acid or a carboxylic acid derivative, such as a carboxylic acid anhydride, a carboxylic acid chloride, a carboxylic acid salt or a carboxylic acid ester. The carboxylic acid in the catalyst typically comprises from 1 to 20 carbon atoms. It preferably comprises 1, 2, 3, 4, 5, 6, 7 or 8 carbon atoms. However, also hetero(poly acids) can be used. The carboxylic acid preferably contains more than 4 carbon atoms in order to make it separable by distillation. An acid or acid derivative having a boiling point greater than that of dichlorohydrin is most suitable. Accordingly, the catalyst typically will have an atmospheric boiling point greater than 175° C., preferably greater than 190° C., more preferably greater than 200° C., since it is typically separable by distillation from a dichlorohydrin, water, and HCl mixture. Generally, the acid or acid derivative is soluble in the reaction medium at the reaction temperature. Preferably, this acid or acid derivative does not form an azeotrope with water.

Particular examples of catalysts are based on at least one carboxylic acid chosen from fatty acids and aromatic carboxylic acids, such as benzoic acid, that are optionally substituted. Other examples of suitable carboxylic acids include poly(carboxylic acids) such as di-, tri- or tetracarboxylic acids.

Dicarboxylic acids are suitably used. In another embodiment, the catalyst is based on substituted benzoic acid. In this embodiment, the aromatic ring often carries at least one substituent in the 2- or 4-position. This substituent is advantageously chosen among the inductive and mesomeric capturing groups such as a nitro group, or among the mesomeric donating and inductive capturing groups such as a hydroxyl group, an alkoxy group, such as a methoxy group, or the halogens such as chlorine and fluorine, or an optionally alkylated amino group, and among these, in particular a di- or trialkylamino group. Specific examples of catalysts are chosen from salicylic acid, 4-chlorobenzoic acid, 2,4-dichlorobenzoic acid, 4-nitrobenzoic acid, and 2,4-dinitrobenzoic acid. In another embodiment, the catalyst is based on a fatty acid. Preferred examples are chosen from valeric acid, caproic acid, heptanoic acid, octanoic (caprylic) acid, lauric acid, decanoic acid, palmitic acid, or mixtures thereof. Octanoic (caprylic) acid is a particularly preferred example of such an acid.

In yet another embodiment, the catalyst is based on a poly(carboxylic acid).

In another embodiment, the catalyst is an organic compound comprising a β-diketone moiety or a β-keto aldehyde moiety as described in our International Patent Application with Appl. No. EP2010/053425.

Of all catalysts mentioned, depending on the circumstances, it may be preferred to use succinic acid, glutaric acid, adipic acid, suberic acid, and/or mixtures thereof. Adipic acid and/or suberic acid may be most preferred.

The catalyst contained in the bottoms of the first distillation step can be economically recycled in the reactor after a purification treatment. For example, catalysts with low solubility in water can be subjected to an acid hydrolysis treatment which is followed by a separation step, e.g. by decantation, filtration or extraction. It has been found that in the case of adipic acid, an acid hydrolysis of the purge leads, after cooling and filtration, to the recovery of crystallized adipic acid of high purity with a good yield.

Pure or purified catalyst can be introduced into the reactor as such or in solution in one of the reactants such as for example glycerol or aqueous hydrochloric acid or in an appropriate solvent, for example selected from water, glycerol monochlorohydrin, and dichloropropanol. Preferably the acid is introduced with as little water and/or solvent as possible, in order to reduce the energy consumption in the distillation step. The addition of the catalyst can be performed continuously or discontinuously.

The catalyst concentration in the reaction medium can suitably be optimized in order to minimize the reaction medium volume. The term "catalyst concentration" is intended to denote the concentration of the acid and its derivatives (esters for instance). The catalyst concentration is expressed in mol of acid and acid derivative, in particular ester moieties per kg of liquid reaction medium. This concentration is generally higher than or equal to 0.1 mol/kg, preferably higher than or equal to 1 mol/kg, and most preferably higher than or equal to 2 mol/kg. The catalyst concentration as defined above is usually lower than or equal to 10 mol/kg, specifically lower than or equal to 8 mol/kg, and more specifically lower than or equal to 4 mol/kg.

The process for producing dichlorohydrin may be carried out in the presence of an organic solvent such as a chlorinated organic solvent, a suitable alcohol, a ketone, an ester or an ether. However, also dichlorohydrin itself or the heavy byproducts formed when making dichlorohydrin from glycerol and hydrogen chloride can be used as a solvent. Using a solvent may reduce the amount of heavy byproducts formed. Particular examples of suitable non-reactive solvents are dichlorohydrin, dioxane, phenol, cresol, and monochlorohydrin (MCH), also known as chlorodihydroxypropane. A mixture of such solvents is also suitable and mixtures of monochlorohydrin and dichlorohydrin are particularly preferred. The effect of the solvent is particularly advantageous if the glycerol content in the reaction medium is less than or equal to 50% by mass relative to the total mass of the reaction medium, and particularly good if this concentration is less than 30%. It is advantageously less than 10% w/w.

If used, the solvent content in the reaction medium is generally from 10 to 95% w/w, preferably from 30 to 80% w/w.

The reaction between glycerin and HCl can be conducted in any conventional way. It is generally carried out at a temperature of at least 20° C. This temperature is preferably at least 60° C., more preferably at least 80° C., and most preferably at least 90° C. The reaction is generally carried out at a temperature of at most 160° C., preferably at most 140° C., and most preferably at most 130° C. However, at a superatmospheric pressure, the reaction temperature can be increased and be as high as 300° C.

The reaction is generally carried out at a pressure of at least 0.3 bara. The reaction is often carried out at a pressure of at least 0.5 bara. In the process according to the invention, the reaction is generally carried out at a pressure of at most 100 bara. This pressure is often at most 20 bara. It is preferably at most 15 bara and most preferably at most 10 bara.

During or after the reaction a distillation is conducted wherein a mixture comprising dichlorohydrin, water, and HCl is obtained as the light fraction.

The process of the present invention is generally carried out in equipment made of conventional suitable materials. Typically this is equipment that is made from or coated with materials that are resistant, under the process conditions, to the chlorinating agents, in particular to hydrogen chloride. By way of suitable material, mention may be made, for example, of enameled steel. Polymers may also be used. Among the polymers, polyolefins such as polypropylene, and in particular fluorinated polymers such as polytetrafluoroethylene, poly(vinylidene fluoride), and poly(perfluoropropylvinylether), and polymers comprising sulphur, such as polysulphones or polysulphides, that are particularly aromatic, are very suitable. Coatings by means of resins can be used effectively; among these, epoxy resins or phenolic resins are particularly suitable. Certain metals or alloys thereof may also be suitable. Mention may in particular be made of tantalum, titanium, copper, gold and silver, nickel and molybdenum, in particular alloys containing nickel and molybdenum. They may be used within the mass, or in the form of cladding, or else by means of any coating process. Ceramics or metalloceramics and refractory materials can also be used. For certain specific equipment, for example heat exchangers, graphite, which is optionally impregnated, is particularly suitable.

In accordance with the invention, further water is added to the mixture comprising dichlorohydrin, water, and HCl, e.g. the reaction mixture as obtained after reacting glycerin and HCl. This further water is added before, during, or both before and during, the distillation step wherein the mixture comprising dichlorohydrin, water, and HCl is separated. The water can be steam, demineralized water, distilled water, or process water, for instance recycled from other parts of the process or from other processes, provided that it does not contain contaminants that interfere in the process or adversely affect the quality of the dichlorohydrin stream and/or the aqueous HCl stream obtained. If the water already contains HCl, it should be in such a quantity that the HCl concentration in the added water is lower than the amount of HCl in the aqueous HCl stream formed in the second distillation step. If the water contains dichlorohydrin, then the maximum amount of dichlorohydrin that is permissible in this stream is the amount of dichlorohydrin present in the water-dichlorohydrin azeotrope at the distillation pressure.

The dichlorohydrin, in particular 1,3-dichloropropane-2-ol, forms a pseudoazeotrope with water and hydrogen chloride. The invention also relates to the processing of such a pseudoazeotropic composition. Such a pseudoazeotropic mixture of dichlorohydrin, water, and HCl is known to be particularly difficult to separate by distillation in a conventional distillation. However, it was found that in accordance with the invention it is well possible, after the addition of an appropriate amount of water to such mixtures, to separate components of the pseudoazeotrope.

Independent of how the mixture comprising dichlorohydrin, water, and HCl is formed, it can be distilled in accordance with the invention such that at least one fraction comprising from 15 to 30% w/w of dichlorohydrin and at most 85, preferably 83, more preferably 80% w/w of water is recovered and at least one other fraction is recovered which contains water, is low in dichlorohydrin, and contains more than 60% w/w, preferably more than 80% w/w, most preferably more than 95% w/w of the HCl that was in the mixture comprising dichlorohydrin, water, and HCl, in a single distillation step. After a liquid/liquid separation of the stream containing the dichlorohydrin, an organic dichlorohydrin fraction is obtained that comprises from 75 to 99.9% w/w, often from 75 to 99% w/w of dichloropropanol and from 0.01 to 25% w/w, often from 1 to 25% w/w of water, both low in HCl.

In another embodiment of the invention, water is added such that a composition is obtained such that it is on the line connecting the water-HCl azeotrope and the dichlorohydrin-water azeotrope in the dichlorohydrin-water-HCl phase diagram at the pressure applied during the distillation (in FIG. 1 depicted by the line D-E, running from the point representing 23% w/w of dichlorohydrin and 77% w/w of water to the point representing a composition with 20% w/w of HCl and 80% w/w of water). The amount of water, i.e. $r_{(H_2O/crude)}$, that needs to be added in that case is $$r_{H_2O/crude} = \frac{x_{DCH\text{-}crude}}{x_{DCH\text{-}az(DCH-H2O)}} + \frac{x_{HCl\text{-}crude}}{x_{HCl\text{-}az(HCl-H2O)}} - 1$$

with $x_{DCH.az(DCH-H2O)}$ being the molar fraction of dichlorohydrin in (heterogeneous) azeotrope of binary system dichlorohydrin-$H_2O$, $x_{DCH.crude}$ being the molar fraction of dichlorohydrin in the crude mixture, $x_{HCl.az(HCl-H2O)}$ being the molar fraction of HCl in (homogeneous) azeotrope of binary system HCl—$H_2O$, and $x_{HCl.crude}$ being the molar fraction of HCl in the crude mixture.

With such compositions the best product streams are obtained at the lowest possible energy input. In another embodiment the composition is such that it is to the right of said line D-E (meaning that more than the optimal amount of water is added), but this may be undesired since it means that either too much water needs to be distilled, resulting in a dichlorohydrin stream which contains more water than desired, and/or the HCl-rich stream formed will be too diluted, making it less valuable. Nevertheless, it may be preferred to use a slight excess of water in order to make sure that essentially all HCl is retrieved in the aqueous HCl stream resulting from the distillation. It is noted that the above numbers are for distillations at atmospheric conditions. At higher pressures, the numbers shift favourably in that the dichlorohydrin stream becomes more concentrated in dichlorohydrin. This means that the amount of water can be reduced accordingly.

Therefore, in another embodiment of the invention, the distillation of the mixture comprising dichlorohydrin, water, HCl is conducted at a pressure above atmospheric pressure. It was found that at increased pressure, slightly more of the water ends up in the aqueous HCl stream and significantly less water ends up in the dichlorohydrin stream. Hence at higher pressures the process to make dichlorohydrin becomes more economic. Accordingly, the pressure during the distillation of the mixture comprising dichlorohydrin, water, HCl is preferably greater than atmospheric (1 bara), more preferably greater than 1.2 bara, even more preferably more than 1.25 bara, more preferably still more than 1.4 bara, and most preferably more than 1.5 bara. The maximum pressure during the distillation is not critical and is determined by the maximum working pressure of the equipment used, energy requirements, and the level of hydrolysis of dichlorohydrin that is accepted, since said hydrolysis increases at the higher temperatures associated with the higher pressures. Accordingly, a pressure less than 15, preferably less than 5 bara, and more preferably less than 3 bara may be preferred.

As said, the dichlorohydrin stream from the distillation of the dichlorohydrin, water, and HCl-comprising mixture will typically subsequently separate into two streams, depending on the composition and the temperature. If so, the dichlorohydrin stream will separate into a dense organic phase and a lighter aqueous phase. Suitably this is done in a decanter or any other liquid/liquid separator. The organic phase contains a considerable amount of dichlorohydrin, for example at least 50% w/w of the total weight of the organic phase, preferably at least 80% w/w, and some water. The aqueous phase contains water and a minority amount of dichlorohydrin, for example at most 50% w/w of the total weight of the aqueous phase, preferably at most 30% w/w. A decantation operation permits separation of the organic phase containing the dichloropropanol from the aqueous phase, this latter may be recycled to the reflux of the distillation or used as is. It is noted that both streams are essentially free of HCl.

The triangular diagram for the ternary mixture DCH—$H_2O$—HCl which is depicted in FIG. 1 is a simple sketch based on pure component data and the compositions of binary azeotropes. The binary azeotropes form distillation boundaries. This means that when starting with a feed stream at one side of the boundary, it is impossible to obtain a product composition at the other side of this boundary by normal distillation. Four distillation regions are distinguished in FIG. 1 (established via residue curve mapping, see for example *Perry's Chemical Engineers' Handbook*, 7$^{th}$ Ed, The McGraw-Hill Companies, Inc. 1997, Chapter 13-56). The distillation step according to the present invention is performed in region 4a, which includes line D-E.

Figure 2:
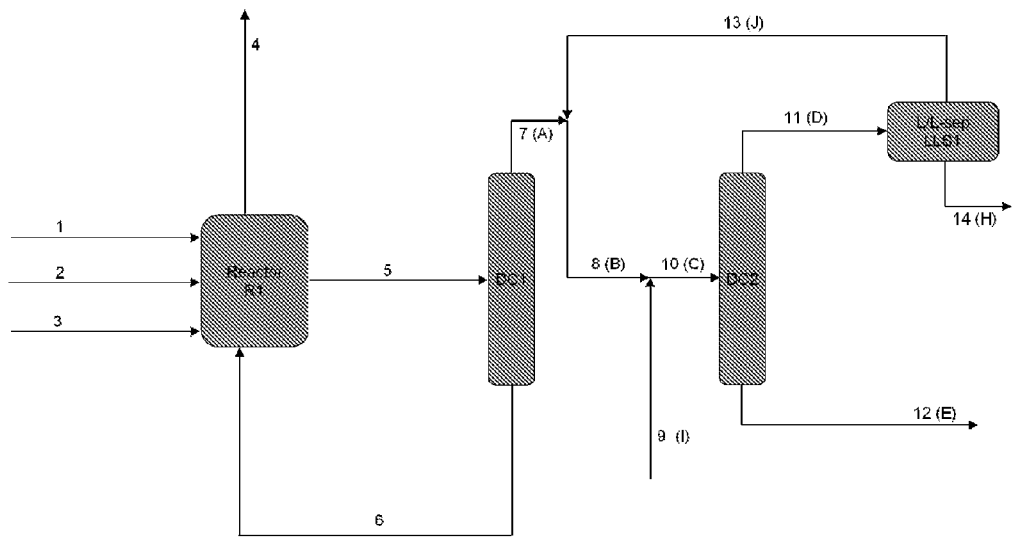
FIG. 2 shows a preferred scheme for a plant that can be used for carrying out the process for producing dichlorohydrin according to the present invention.

The letters in FIG. 2 correspond to the points indicated in FIG. 1.

FIG. 2 shows a more preferred scheme for a plant that can be used for carrying out the process for producing dichlorohydrin according to the invention. The dichlorohydrin stream and the heavy product stream of the reaction between glycerin and HCl are separated in DC1, where the dichlorohydrin, water, and HCl can be withdrawn at the top via line (7), the catalyst and the heavy products can be withdrawn at the bottom via line (6), and which are optionally recycled to the reactor (R1). The column (DC1) preferably functions at a subatmospheric pressure. Depending on the circumstances a pressure of 0.1-0.5 bara may be preferred.

Accordingly, FIG. 2 presents a particular embodiment of the present invention wherein stream (1) represents a stream containing glycerol, a derivative thereof or a combination of both, which is fed to a reactor (R1). As the skilled person will understand, the reactor can also consist of a series of reactors, or another configuration of reactors. Stream (2) comprises HCl. The HCl stream can be dry (gas) or wet (aqueous solution). Stream (3) is optional and comprises one or more conventional catalysts, such as organic acids, preferably diacids, or ketones/aldehydes, preferably beta-diketones. The process conditions in the reactor R1 are conventional. Stream (4) is vent gas leaving the reactor comprising amongst others HCl and non-condensables. Stream (5) is a mixture of reactants, intermediates, products, and catalyst that is directed to a first separation step (DC1), where it is split into a light crude product (7) and a heavy stream (6) which is optionally wholly or partly re-used, by recycling to the reactor (R1).

The light crude product stream (7) comprises dichlorohydrin, water, and HCl. Any person skilled in the art would recognize that the reactor and the separation DC1 may be combined in a single apparatus.

The present invention relates to the isolation of dichlorohydrin from the crude product stream (7) separately or in combination with the previous steps. The crude stream (7) is optionally mixed with a recycle stream (12) from a liquid/liquid-separator (LLS1) and fed to a distillation column (DC2) together with a stream comprising water (9). Any person skilled in the art would recognize that the streams may be mixed or fed to the separation DC2 in any specific order.

The column DC2 produces a hydrochloric acid stream free of dichlorohydrin (12) and a dichlorohydrin-rich stream free of HCl (11).

It is worth noting that the high boiling component dichlorohydrin is obtained as top product, while the low boiling HCl is obtained as bottom product. This quite contradicts what is considered normal in a distillation process, where the high boiling component is obtained from the bottoms flow and the light boiling component is obtained in the distillate.

Preferably the dichlorohydrin-rich stream (11) is then further processed in a liquid-liquid separator (LLS1), such as a decanter, where it is split into a water phase and an organic phase. The stream containing the water phase, which is poor in dichlorohydrin (13), can be recycled to the distillation column (DC2). The stream of the organic phase (14) is the desired final product that contains dichlorohydrin and a minor amount of water. Depending on its usage this product stream may be subjected to an optional water removal step.

The stream of hydrochloric acid (12) obtained from DC2 is a valuable byproduct as it can be obtained at azeotropic composition, depending on the amount of water present in the stream (10) to the distiller (DC2) and the distillation conditions of DC2.

The distillation or evaporation operation can be carried out either by means of distillation columns or by means of evaporators, film evaporators or alternatively wiped thin film evaporators. The recoverable fractions of the residues can be separated advantageously by means of a wiped thin film evaporator with an interior or exterior condenser.

In a particular embodiment, the dichlorohydrin as obtained in accordance with the invention is used in a dehydrochlorination process in the presence of at least one other alcohol, more particularly in the presence of polyols, such as, for example, bisphenol A, so as to obtain "epoxy" resins or usable monomers thereof. This use may be particularly preferred for dichlorohydrin with a high content of 1,3 dichloropropanol, since it makes it possible to conserve a linear structure of the polymer or monomer thus obtained.

The invention also relates to the use of a dichloropropanol containing at least 50% w/w of 1,3-dichloropropane-2-ol relative to the total dichloropropanol, as starting product for producing organic compounds such as, in particular, epichlorohydrin or epoxy resins. In this use, the 1,3-dichloropropane-2-ol content is often greater than or equal to 75% w/w relative to the total dichloropropanol. Preferably, this content is greater than or equal to 80% w/w. Good results have been obtained with a dichloropropanol containing at most approximately 99% w/w, or even at most approximately 95% w/w of 1,3-dichloropropane-2-ol relative to the total amount of dichlorohydrin. It is also possible to use dichlorohydrin consisting essentially of 1,3-dichloropropane-2-ol.

In a particular embodiment, the dichlorohydrin as obtained in accordance with the invention is used in the dehydrochlorination process so as to obtain epichlorohydrin.

The process according to the present invention is further illustrated by the following example.

EXAMPLE

A synthetic crude mixture was made by mixing 165.2 grams of DCH and 54.2 grams of HCl-36 (an aqueous solution of 36.0% w/w HCl). The resulting crude mixture consisted of 3.743 moles, of which 34.2 mol % was DCH and 14.3 mol % HCl. The molar amount of water to be added to 1 mol of said mixture ($r_{(H_2O/crude)}$) was calculated as follows for the distillation at 1 bar, using the azeotropic composition data at 1 bar as listed in Tables 2 and 3:

$$r_{H_2O/crude} \geq \frac{34.22}{4.17} + \frac{14.31}{10.83} - 1 = 8.53$$

From this calculation it was concluded that the minimum amount of water to be added was 31.9 moles or 575.1 grams.

In practice 776.9 grams of water were added, meaning an actual ratio of 11.5 moles of water added to 1 mol of crude mixture. The mixture thus obtained weighed 997 grams, with a composition of 1.96% w/w HCl, 16.57% w/w dichlorohydrin, and 81.47% w/w H$_2$O, which is located in the desired region 4a of FIG. 1, not on the line D-E in the diagram, but to the right of it.

Next the 997 grams of liquid were transferred to a rotating evaporator and distilled (without reflux) at atmospheric pressure. The distillate that was obtained mainly consisted of dichlorohydrin and H$_2$O, and was separated, in a decanter, into an aqueous and an organic phase. Both phases were analyzed and the overall composition of the distillate was determined.

Table 1 represents the total amount of distillate that was obtained in time and the total amount of the components present in the distillate. Units in grams.

TABLE 1

| Mass | Dichlorohydrin | HCl | H$_2$O |
|---|---|---|---|
| 91.6 | 18.32 | 0.00 | 73.28 |
| 186.8 | 38.31 | 0.00 | 148.49 |
| 301.7 | 60.60 | 0.00 | 241.10 |
| 401.1 | 80.68 | 0.00 | 320.42 |
| 502.1 | 100.07 | 0.00 | 402.03 |
| 600.9 | 118.06 | 0.00 | 482.85 |
| 697.3 | 132.80 | 0.02 | 564.48 |
| 796.8 | 142.16 | 0.05 | 654.59 |
| 838.2 | 143.48 | 0.08 | 694.64 |

Surprisingly the high boiling dichlorohydrin was obtained as the top product. Despite the fact that conditions are far from optimal due to absence of a reflux, dichlorohydrin is obtained at high yield with only a low amount of HCl.

TABLE 2

Azeotropic composition of H$_2$O-dichlorohydrin

| Pressure [mbara] | Temperature [° C.] | dichlorohydrin fraction [% w/w dichlorohydrin] | dichlorohydrin fraction [mol % dichlorohydrin] |
|---|---|---|---|
| 150 | 53.5 | 18.14 | 3.00 |
| 1,000 | 98.4 | 23.75 | 4.17 |
| 2,000 | 118.5 | 26.22 | 4.73 |
| 5,000 | 149.3 | 28.93 | 5.38 |

TABLE 3

Azeotropic composition of H$_2$O—HCl

| Pressure [mbara] | Temperature [° C.] | HCl fraction [% w/w HCl] | HCl fraction [mol % HCl] |
|---|---|---|---|
| 200 | 69.956 | 22.520 | 12.56 |
| 333 | 81.205 | 21.883 | 12.16 |
| 493 | 90.237 | 21.365 | 11.84 |
| 533 | 92.080 | 21.235 | 11.76 |
| 600 | 95.029 | 21.075 | 11.66 |
| 667 | 97.578 | 20.916 | 11.56 |
| 720 | 99.653 | 20.777 | 11.47 |
| 800 | 102.209 | 20.638 | 11.39 |
| 853 | 103.967 | 20.507 | 11.31 |
| 907 | 105.564 | 20.413 | 11.25 |
| 933 | 106.424 | 20.360 | 11.22 |
| 987 | 107.859 | 20.268 | 11.16 |
| 1,013 | 108.584 | 20.222 | 11.13 |
| 1,067 | 110.007 | 20.155 | 11.09 |
| 1,333 | 116.185 | 19.734 | 10.83 |
| 1,627 | 122.980 | 19.358 | 10.61 |

Source: W. Bonner and R. Wallace, *The boiling points of constant boiling hydrochloric acids. J. Am. Chem. Soc.*, 52, 1747-1750 (1930).

Azeotropic compositions at other temperatures can be obtained by proper inter- and extrapolation.

These data show that increasing the pressure improves the energy efficiency of the separation process.

The invention claimed is:

1. A process to make a dichlorohydrin-rich product, comprising:
    a first step, wherein glycerin is reacted with HCl in the presence of a catalyst and optionally in the presence of a solvent;
    a second step, wherein the reaction mixture of the first step is separated into a light liquid stream comprising dichlorohydrin, water and HCl, and a stream of heavy compounds including the catalyst; and
    a distillation step wherein the light liquid stream is used as a crude mixture which is separated into a first product stream which is rich in dichlorohydrin and low in HCl, and a second product stream which is an aqueous HCl-containing composition low in dichlorohydrin, and wherein an amount of water is added before, during, or both before and during, the distillation step, with the molar amount of water which is added to 1 mol of the mixture ($r_{H_2O/crude}$) being $$r_{H_2O/crude} \geq \frac{x_{DCH\text{-}crude}}{x_{DCH\text{-}az(DCH-H2O)}} + \frac{x_{HCl\text{-}crude}}{x_{HCl\text{-}az(HCl-H2O)}} - 1$$

with $x_{DCH.az(DCH-H2O)}$ being the molar fraction of dichlorohydrin in (heterogeneous) azeotrope of binary system dichlorohydrin-H$_2$O, $x_{DCH.crude}$ being the molar fraction of dichlorohydrin in the crude mixture, $x_{HCl.az(HCl-H2O)}$ being the molar fraction of HCl in (homogeneous) azeotrope of binary system HCl—H$_2$O, and $x_{HCl.crude}$ being the molar fraction of HCl in the crude mixture.

2. The process according to claim 1, wherein the water concentration during the distillation step is on the line connecting the water-HCl azeotrope and the dichlorohydrin-water azeotrope in a dichlorohydrin-water-HCl phase diagram at the pressure applied during the distillation step.

3. The process according to claim 1, wherein the distillation step is conducted at a pressure between 1.2 and 15 bar absolute.

4. The process according to claim 1, further comprising a separation step wherein the first stream which is rich in dichlorohydrin and low in HCl is separated into an organic stream rich in dichlorohydrin and an aqueous dichlorohydrin stream low in dichlorohydrin.

5. The process according to claim 3, further comprising a separation step wherein the first stream which is rich in dichlorohydrin and low in HCl is separated into an organic stream rich in dichlorohydrin and an aqueous dichlorohydrin stream low in dichlorohydrin.

6. The process according to claim 4, wherein the aqueous dichlorohydrin stream is wholly or partially recycled and added to the crude mixture, in which process the water in the stream may be the sole source of water that is added or may be part of the water that is added.

7. The process according to claim 5, wherein the aqueous dichlorohydrin stream is wholly or partially recycled and added to the crude mixture, in which process the water in the stream may be the sole source of water that is added or may be part of the water that is added.

8. The process according to claim 1, wherein at least 50% of all the dichlorohydrin in the crude mixture is present in the first product stream which is rich in dichlorohydrin and low in HCl.

9. The process according to claim 3, wherein at least 50% of all the dichlorohydrin in the crude mixture is present in the first product stream which is rich in dichlorohydrin and low in HCl.

10. The process according to claim 4, wherein at least 50% of all the dichlorohydrin in the crude mixture is present in the first product stream which is rich in dichlorohydrin and low in HCl.

11. The process according to claim 5, wherein at least 50% of all the dichlorohydrin in the crude mixture is present in the first product stream which is rich in dichlorohydrin and low in HCl.

12. The process according to claim 1, wherein the stream of heavy compounds is recycled to the first step wherein glycerin is reacted with HCl.

13. The process according to claim 3, wherein the stream of heavy compounds is recycled to the first step wherein glycerin is reacted with HCl.

14. The process according to claim 4, wherein the stream of heavy compounds is recycled to the first step wherein glycerin is reacted with HCl.

15. The process according to claim 5, wherein the stream of heavy compounds is recycled to the first step wherein glycerin is reacted with HCl.

16. The process according to claim 8, wherein the stream of heavy compounds is recycled to the first step wherein glycerin is reacted with HCl.

17. The process according to claim 9, wherein the stream of heavy compounds is recycled to the first step wherein glycerin is reacted with HCl.

18. The process according to claim 11, wherein the stream of heavy compounds is recycled to the first step wherein glycerin is reacted with HCl.

19. The process according to claim 1, wherein the reaction mixture of the first step is separated in the second step into, a light liquid stream that is essentially free of catalyst and comprises dichlorohydrin, water, and HCl, and a stream of heavy compounds.

20. The process according to claim 19, wherein the second step is performed at a pressure below atmospheric pressure.

* * * * *